United States Patent [19]

Knapp et al.

[11] Patent Number: 5,955,090
[45] Date of Patent: *Sep. 21, 1999

[54] **IMMUNOGENIC HYBRID PROTEIN OPRF-OPRI DERIVED FROM *PSEUDOMONAS AERUGINOSA* MEMBRANE PROTEINS**

[75] Inventors: Bernhard Knapp, Wetter; Klaus-Dieter Hungerer; Michael Bröker, both of Marburg; Bernd-Ulrich von Specht, Bahlingen/Kaiserstuhl; Horst Domdey, Neuried, all of Germany

[73] Assignee: Chiron Behring GmbH & Co., Marburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/572,447

[22] Filed: Dec. 14, 1995

[30] Foreign Application Priority Data

Dec. 16, 1994 [EP] European Pat. Off. ............ P 94120023

[51] Int. Cl.⁶ .................................................. A61K 39/108
[52] U.S. Cl. ..................................... 424/260.1; 424/184.1; 424/185.1; 424/190.1; 424/192.1; 424/193.1; 424/194.1; 424/197.11; 424/200.1; 424/234.1; 424/823; 424/824; 424/825; 424/826; 424/828; 424/829; 435/41; 435/42; 435/69.1; 435/172.1; 435/172.2; 435/172.3; 435/243; 435/252.1; 435/252.3; 435/252.34; 435/320.1
[58] Field of Search ............................. 424/184.1, 185.1, 424/190.1, 192.1, 193.1, 194.1, 197.11, 200.1, 234.1, 260.1, 823, 824, 825, 826, 828, 829; 435/41, 42, 69.1, 172.1, 172.2, 172.3, 243, 252.1, 252.3, 252.34, 320.1

[56] References Cited

FOREIGN PATENT DOCUMENTS

| | | |
|---|---|---|
| 0 297 291 B1 | 1/1989 | European Pat. Off. . |
| 0 357 024 A2 | 3/1990 | European Pat. Off. . |
| WO 93/24636 | 12/1993 | WIPO . |
| WO 93/24636 | 12/1996 | WIPO . |

OTHER PUBLICATIONS

Hughes et al., "Synthetic Peptides Representing Epitopes of Outer Membrane Protein F of *Pseudomonas Aeruginosa* That Elicit Antibodies Reactive with Whole Cells of Heterologous Immunotype Strains of *P. Aeruginosa*", Infect. Immun., 60(9):3497–3503 (1992).

Finke et al., "Protection Against Experimental *Pseudomonas Aeruginosa* Infection by Recombinant *P. Aeruginosa* Lipoprotein I Expressed in *Escherichia Coli*", Infect. Immun., 58(7):2241–2244 (1990).

Duchene et al., "Sequence and Transcriptional Start Site of the *Pseudomonas Aeruginosa* Outer Membrane Porin F Gene", J. Bacteriol., 170(1)155–162 (1988).

US005955090A

Duchene et al., "*Pseudomonas Aeruginosa* Outer Membrane Liproprotein I Gene: Molecular Cloning, Sequence, and Expression in *Escherichia Coli*", J. Bacteriol., 171(8):4130–4137 (1989).

Roussilhon et al., "Responses of T Cells From Sensitized Donors to Recombinant and Synthetic Peptides Corresponding to Sequences of the *Plasmodium Falciparum* SERP Antigen", Immunol. Lett., 25:149–154 (1990).

Johnson et al., "Improved Technique Utilizing Nonfat Dry Milk for Analysis of Proteins and Nucleic Acids Transferred to Nitrocellulose", Gene Anal. Techn., 1:3–8 (1984).

Schorr et al., "Surface Expression of Malarial Antigens in *Salmonella Typhimurium*: Induction of Serum Antibody Response Upon Oral Vaccination of Mice", Vaccine, 9:675–681 (1991).

Horton et al., "Engineering Hybrid Genes Without The Use of Restriction Enzymes: Gene Splicing by Overlap Extension", Gene, 77:61–68 (1989).

Baldari et al., "A Novel Leader Peptide Which Allows Efficient Secretion of a Fragment of Human Interleukin 1β in *Saccharomyces Cerevisiae*", EMBO. J., 6(1):229–234 (1987).

Finke et al., "Protection of Immunosuppressed Mice Against Infection With *Pseudomonas Aeruginosa* by Recombinant *P. Aeruginosa* Lipoprotein I and Lipoprotein I–Specific Monoclonal Antibodies", Infect. Immun., 59(4):1251–1254 (1991).

Finnen et al., "Analysis of the *Pseudomonas aeruginosa* Major Outer Membrane Protein OprF by Use on Truncated OprF Derivatives and Monoclonal Antibodies", J. Bacteriol, 174(15):4977–4985 (1992).

Von Specht et al., "Outer Membrane Proteins of *Pseudomonas aerunginosa* as Vaccine Candidates", Behring Inst. Mitt., 95:85–96 (1994).

v. Specht, B.–U., et al., "Outer Membrane Proteins of *Pseudomonas Aeruginosa* as Vaccine Candidates," Behring Inst. Mitt., vol. 95, pp. 85–96.

Finnen, Renee L., et al., "Analysis of the *Pseudomonas aeruginosa* Major Outer Membrane Protein OprF by Use of Truncated OprF Derivatives and Monoclonal Antibodies," J. Bacteriol. 174(15):4977–4985 (Aug. 1992).

(List continued on next page.)

*Primary Examiner*—James C. Housel
*Assistant Examiner*—Bao-Thuy L. Nguyen
*Attorney, Agent, or Firm*—Robins & Associates; Alisa A. Harbin; Robert P Blackburn

[57] ABSTRACT

The present invention relates to a hybrid protein comprising the *Pseudomonas aeruginosa* outer membrane protein I (OprI) which is fused with its amino terminal end to the carboxy-terminal end of a carboxy-terminal portion of the *Pseudomonas aeruginosa* outer membrane protein F (OprF), as well as to monoclonal or polyclonal antibodies against this hybrid protein. Both, the hybrid protein and the antibodies directed to the hybrid protein confer protection against an infection by *Pseudomonas aeruginosa* to laboratory animals or man.

6 Claims, 4 Drawing Sheets

OTHER PUBLICATIONS

Finke, M. et al., "Protection of Immunosuppressed Mice against Infection with *Pseudomonas aeruginosa* by a Recombinant *P. aeruginosa* Lipoprotein I and Lipoprotein I–Specific Monoclonal Antibodies," Infect. and Immun. 59(4):1251–54 (Apr. 1991).

Hughes, Eileen E., et al., "Synthetic Peptides Representing Epitopes of Outer Membrane Protein F of *Pseudomonas aeruginosa* That Elicit Antibodies Reactive with Whole Cells of Heterologous Immunotype Strains of *P. aeruginosa*," Infect. and Immun. 60(9):3497–3503 (Sep. 1992).

IMMUNOGENIC HYBRID PROTEIN OPRF-OPRI DERIVED FROM *PSEUDOMONAS AERUGINOSA* MEMBRANE PROTEINS

FIELD OF THE INVENTION

The present invention relates to a hybrid protein comprising the *Pseudomonas aeruginosa* outer membrane protein I. (OprI or OMPI) which is fused with its amino terminal end to the carboxy-terminal end of a carboxy-terminal portion of the *Pseudomonas aeruginosa* outer membrane protein F (OprF or OMPF), as well as to monoclonal or polyclonal antibodies against this hybrid protein. Both, the hybrid protein and the antibodies directed to the hybrid protein confer protection against an infection by *Pseudomonas aeruginosa* to laboratory animals or man.

BACKGROUND OF THE INVENTION

*Pseudomonas aeruginosa* is an opportunistic gram-negative pathogen. It represents a major course of hospital-aquired infections, especially in burnt and other immuno-compromised patients, including transplant or cancer patients. Therefore, it is regarded as a "problem microbe" in human medicine.

Many efforts have been made so far in order to develop a vaccine against *Pseudomonas aeruginosa*. For example, in the EP-0 297 291 the complete amino acid sequence of the outer membrane protein F, as well as the nucleotide sequence coding for OprF is disclosed. In the EP-0 357 024 the complete amino acid sequence of the outer membrane protein I and, additionally, the nucleotide sequence coding for OprI is shown. Furthermore, with both proteins it was shown that they may be useful for conferring immunoprotection against *Pseudomonas aeruginosa* to an animal or human proband. However, improvement of procedures of vaccination against a lethal *Pseudomonas aeruginosa* infection is still an object.

SUMMARY OF THE INVENTION

Surprisingly, it was found by the inventors that a hybrid protein, wherein OprI is linked with its N-terminal end to a C-terminal portion of OprF is significantly more immunogenic than fusion proteins only comprising OprI or OprF or mixtures of the latter fusion proteins.

Thus, the present invention relates to a hybrid protein comprising the *Pseudomonas aeruginosa* outer membrane protein I which is fused with its amino-terminal end to the carboxy-terminal end of a carboxy-terminal portion of the *Pseudomonas aeruginosa* outer membrane protein F, said carboxy-terminal portion comprising the sequence from aa 190 to aa 350. In a preferred embodiment said carboxy terminal portion is the sequence from aa 190 to aa 342.

The present invention further relates to a hybrid protein comprising the *Pseudomonas aeruginosa* outer membrane protein I which is fused with its amino terminal end to the carboxy-terminal end of a carboxy-terminal portion of the *Pseudomonas aeruginosa* outer membrane protein OprF, wherein said carboxy-terminal portion comprises one or more of the surface-exposed B-cell epitopes SEE 1, SEE 2, SEE 3 and SEE 4. These B-cell epitopes are located at the following amino acid (aa) positions of the OprF: SEE 1=aa 212–240, SEE 2=aa 243–256, SEE 3=aa 285–298 and SEE 4=aa 332–350 (see example 1 and Hughes et al. (1992), Infect. Immun. 60, pp. 3497–3503).

Another embodiment of the present invention is a vaccine comprising at least one of the above-mentioned hybrid proteins.

Moreover, the present invention relates to monoclonal or polyclonal antibodies directed to one or more of the above hybrid proteins. These antibodies may also be used in a vaccine in order to confer passive protection against an infection by *Pseudomonas aeruginosa* to a subject.

Further aspects of the present invention are nucleic acids which are coding for the above-mentioned hybrid proteins.

Additionally, the present invention relates to a process for the preparation of the above-mentioned hybrid proteins, which comprises bringing about the expression of a nucleic acid as mentioned above, which is coding for a hybrid protein according to the invention, in pro- or eukaryotid cells.

The invention is further explained in detail in the examples which follow and in the claims.

■ signal sequence of *Kluyveromyces lactis* killer toxin.   ● potential glycosylation site
▨ GST (aa 1–225)    ▥ OprF (aa 190–350)
▤ OprF (aa 190–342)    ▦ OprI (aa 21–83)

Figure 2:
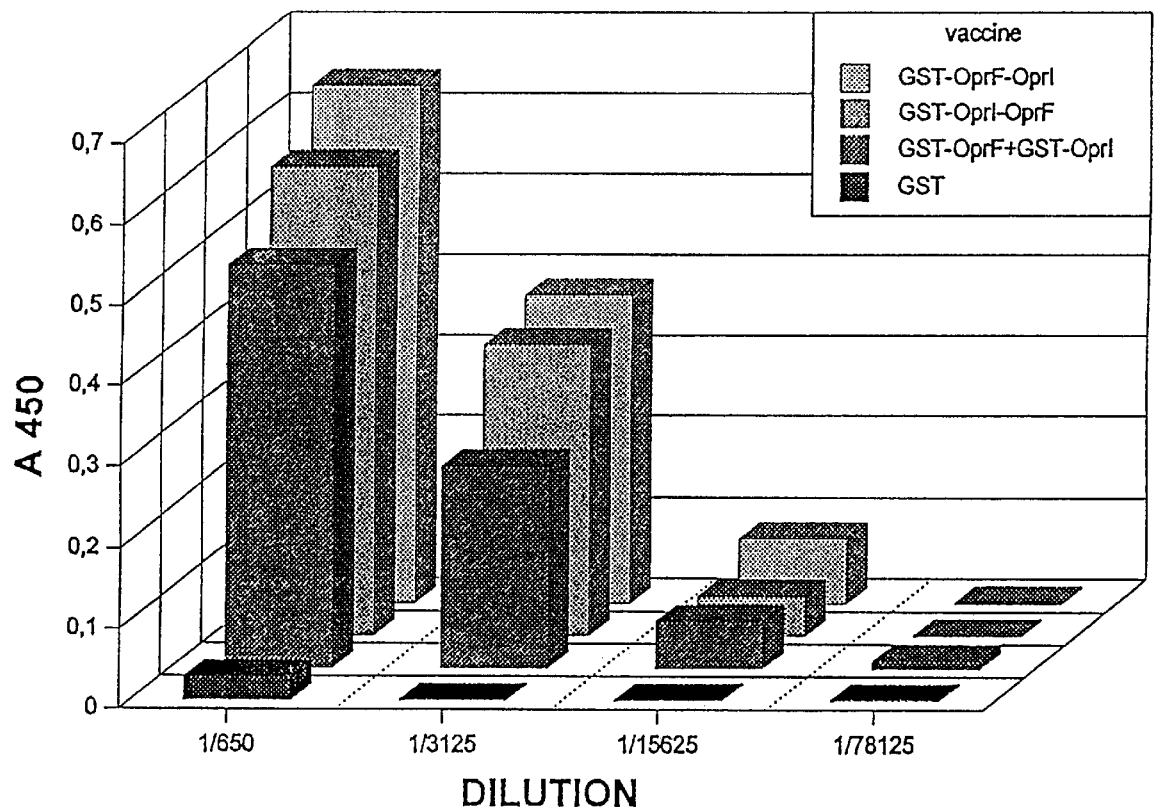

FIG. 2 is a determination of antibody titers against *P. aeruginosa* in sera of mice immunized with the indicated GST linked recombinant outer membrane vaccine or with GST alone. ELISA measurements were carried out on plates coated with sonicated *P. aeruginosa* serogroup 12.

Figure 3:
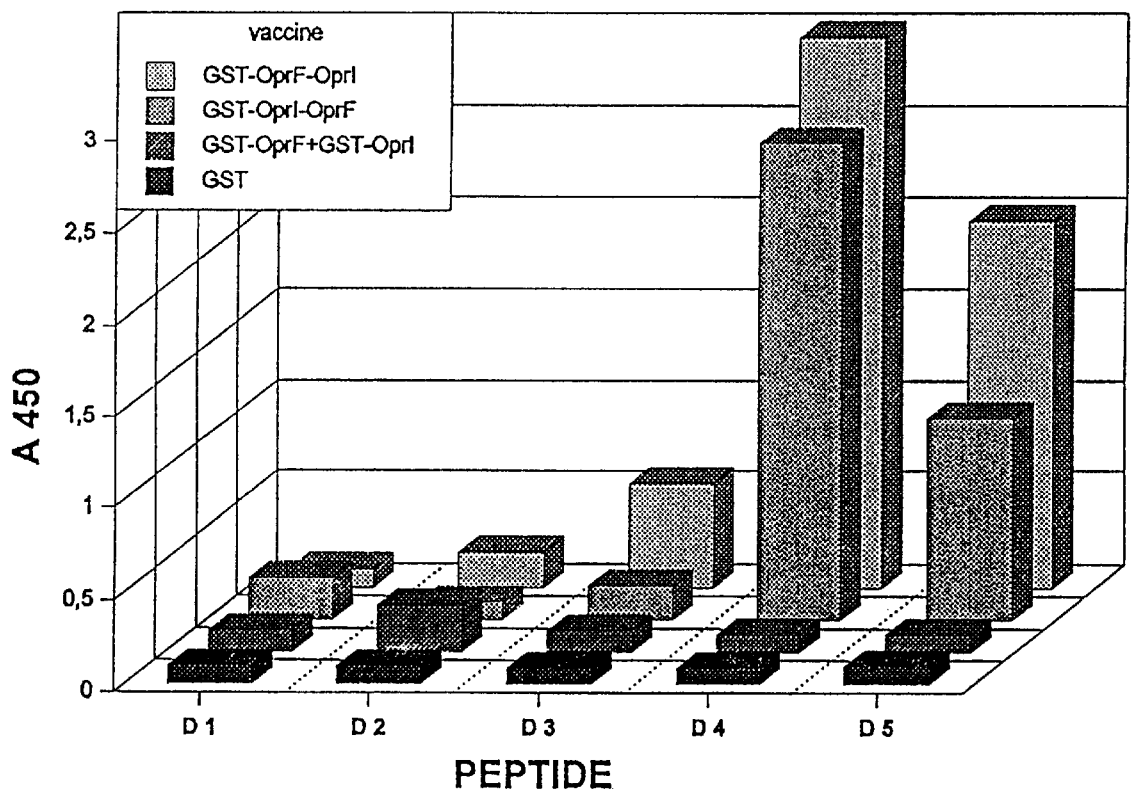

FIG. 3 is a antibody determination by ELISA against synthetic peptides D1–D5 listed in Table 1, which represent B-cell epitopes of OprF. Mice were immunized four times with the indicated recombinant fusion proteins or GST alone.

Figure 4:
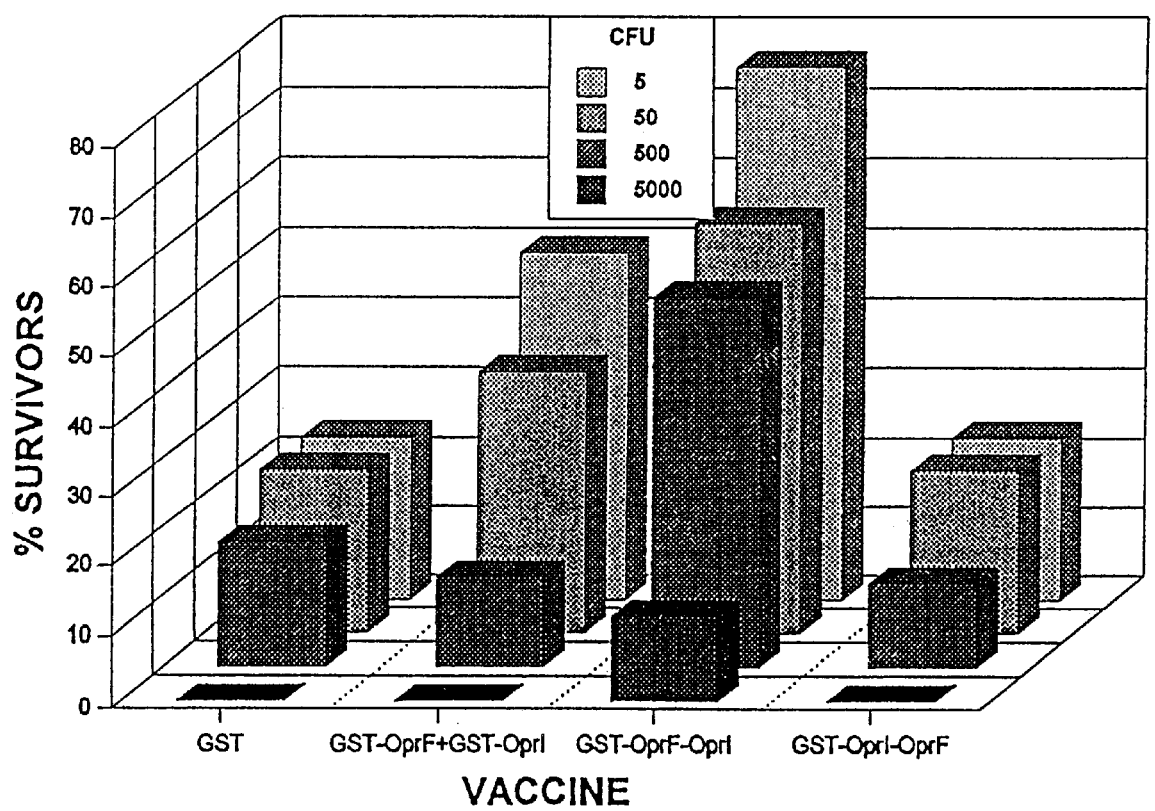

FIG. 4 demonstrates survival of BALB/c mice after immunization with the indicated vaccine or GST alone, followed by immunosuppression and intraperitoneal challenge with 5, 50, 500, or 5000 colony forming units of *P. aeruginosa* serogroup 1. Bars represent percentage of survivors (n=16–17) per challenge dose.

DETAILED DESCRIPTION OF THE INVENTION

In the following the sources of the microorganisms and the DNAs as well as methods that were used in the following examples, and which are for example regarded useful for carrying out the invention are indicated.

Microorganisms: *P. aeruginosa* International Antigenic Typing Scheme serogroup I (ATCC 33348) was obtained from A. Bauernfeind, Max. von PettenkoferInstitut, University of Munich. Bacteria were grown and adjusted to the required concentration as previously described (Finke, M. et al. (1990), Infect. Immun., 58, pp. 2241–2244). For the expression of recombinant proteins *E. coli* K-12 W3110 lacI$^Q$L8 was used. For expression of OPRs in yeast we used *Saccharomyces cerevisiae* strain HT393 (leu2, ura3 pra1, prb1, prc1, pre1, cps1).

Source of DNAs: Three recombinant plasmids were used as the source of DNAs: pFSauI, a pUC19 derived plasmid that contains a 1,0 kb Sau 3Al-fragment of the *P. aeruginosa* outer, membrane protein F gene encoding the C-terminal part of the protein from amino acid positions 57 to 350 (Duchêne, M. et al. (1988), J. Bacteriol. 170, pp. 155–162); pITaq1, a pUC19 derived plasmid that contains a 626 bp Taq1-fragment spanning the complete OprI gene (Duchêne, M. et al. (1989), J. Bacteriol. 171, pp. 4130–4137), and the expression vector pGEX-2a originating from the vector pGEX-2T modified by the introduction of the polylinker from vector pTRC. The vector pGEX-2a contains the tac promoter followed by the coding sequence for 26 kDa Schistosoma japonicum glutathione-S-transferase, a cleavage site for thrombin and the pTRC specific polylinker region.

Characterization of antisera induced against synthetic peptides: Synthetic peptides representing amino acid regions 190–213 (D1), 212–240 (D2, SEE 1), 239–250 (D3), 284–316 (D4), and 332–350 (D5, SEE 4) from OprF were synthesized as described in (Roussilhon, C. E. et al. (1990) Immunol. Lett. 25, pp. 149–154). Rabbits were immunized subcutaneously at eight different locations near, lymph nodes with 200 µg KLH conjugated peptide in complete Freund's adjuvant, and reimmunized two weeks later with 400 µg of the conjugate in incomplete Freund's adjuvant. The animals received two booster injections intravenously of 150 µg and 100 µg of conjugate six and nine weeks after the first immunization. Antibody titers against peptides were measured by ELISA on plates coated with 5 ng per ml of peptide solution in 50 mM sodium phosphate buffer, pH 7.5 (PBS) overnight at room temperature. Plates were washed three times with 0.05 M citric acid and 0.05 M Tris, pH 7.4, and then dried over silica gel for 3 days. Rabbit sera were diluted 1:160 and saturated with, E. coli proteins. Western blot analysis with recombinant GST fusion-proteins and immunofluorescence determinations against intact P. aeruginosa serogroup 11 (ATCC 33358) were carried out by a method reported in the literature (Johnson, D. A. et al. (1984) Gene Anal. Techn. 1, p. 3–8), Schnorr, J. B. et al. (1991), Vaccine 9, pp. 675–681).

Expression of OprF and OprI as gluthation-S-transferase fusion proteins: The oligonucleotides p1 (5'-AAA GAG CTC GCT CCG GCT CCG GAA CCG GTT GCC GAC-3') (SEQ ID NO: 1) with a SacI restriction site at the 5' end, corresponding to bases 568 to 594 of the OprF gene, and p2, (5'-AAA AAG CTT ACT TGG CTT CGG CTT CTA CTT CGG-3') (SEQ ID NO: 2) with a HindIII restriction site at the 5' end, complementary to bases 1028 to 1053 of the OprF gene, and 10 ng of the plasmid pFSau1 were employed for a polymerase chain reaction, using the Perkin Elmer Cetus Gen-Amp Kit, which yielded a 500 bp fragment. The amplified fragment was digested with SacI and HindIII and introduced into the vector pGEX-2a to obtain plasmid pGEX-OprF, which encodes the C-terminal part of the porin OprF from amino acids 190 to 350. The-oligonucleotides p3 (5'-CGT ACC ATG GTG AGC AGC CAC TCC AAA GAA ACC GAA GCT-3'), (SEQ ID NO: 3) with an NcoI rescriction site at the 5' end corresponding to bases 61 to 87 of the coding region of the OprI gene, and p4 (5+-AAA AAG CTT CTA TTA CTT GCG GCT GGC TTT TTC C-3'), (SEQ ID NO: 4) with a HindIII restriction site at the 5' end complementary-to bases 231 to 255 of the coding region of the OprI gene, and 10 ng of the plasmid DNA pITaq1 were used in a polymerase chain reaction to amplify a 215 bp fragment, which was then treated with the restriction enzymes NcoI and HindIII to introduce it into the corresponding sites of the expression vector pGEX-2a, in order to obtain plasmid pGEX-OprI, which encodes amino acids 21 to 83 of OprI.

Construction of the GST-OprI-OprF and GST-OprF-OprI hybrid genes: The oligonucleotides p1 (see above) and p5 (5'-TTC AAC GCG ACG GTT GAT AGC GCG-3') (SEQ ID NO: 5) (which is complementary to bases 1003 to 1026 of the OprF gene) and 10 ng of the plasmid pFSau1 were used to amplify a 470 bp OprF fragment. A second polymerase chain reaction was carried out with 10 ng of plasmid pITaq1 and the oligonucleotides p4 (see above), and p6 (5'-GAA GGC CGC GCT ATC AAC CGT CGC GTT GAA AGC AGC CAC TCC AAA GAA ACC GAA GCT-3') (SEQ ID NO: 6), in which nucleotides 1 through 30 correspond to bases 997 to 1026 of the OprF gene and nucleotides 31 through 57 correspond to bases 61 through 87 of the OprI coding region. This yielded a 240 bp fragment. 150 ng of both obtained DNA fragments and oligonucleotides p1 and p4 were used for a third polymerase chain reaction as described by Horton (Horton, R. M. et al. (1989), Gene 77, pp. 61–68). The obtained 660 bp fragment was digested with the restriction endonucleases SacI and HindIII, and introduced into the vector pGEX-2a to obtain plasmid pGEX-OprF-OprI, which encodes amino acids 190 to 342 of OprF and amino acids 21 to 83 of OprI. The oligonucleotides p3 and p7 (5'-AAA GAG CTC CTT GCG GCT GGC TTT TT CAG CAT GCG-3') (SEQ ID NO: 7) with a SacI restriction site at the 5' end, complementary to bases 223 to 249 of the coding region from the OprI gene, and 10 ng of plasmid pITaq1 were used to amplify a 210 bp fragment, which was introduced into the vector pGEX2a with the help of the restriction enzymes NcoI and SAcI. The obtained plasmid was digested with the enzymes SacI and HindIII to introduce a 490 bp fragment obtained by digestion of the plasmid pGEX-OprF, using the corresponding enzymes; Plasmid pGEX-OprI-OprF encodes amino acids 21 to 83 from OprI and amino acids 190 to 350 from OprF, which are separated by a two amino acid linker introduced at the SacI cloning site.

Expression and purification of the recombinant proteins in E. coli: The four plasmids pGEX-OprF, pGEX-OprI, pGEX-OprF-OprI and pGEX-OprI-OprF were transformed into the E. coli K-12 strain W3110 lac I$^Q$L8. For large scale antigen production, 5-liter bacterial cultures containing the plasmids were left to grow to $OD_{660}$=1 and the expression of the P. aeruginosa specific recombinant antigens induced by isopropylthiogalactoside. After disruption of the cells the four different glutathione-S-transferase fusion proteins were found to be soluble in aqueous solutions. Therefore, the four fusion proteins could be purified from crude bacterial lysates under non-denaturing conditions by affinity chromatography on immobilized glutathione to a purity of about 80%.

Active immunization and protection experiments: 4 groups (A–D) of 68 female BALB/c Mice (10–12 weeks old) each received 100 µg of antigen: GST (A), GST-OprF+GST-OprI (B), GST-OprF-OprI (C) or GST-OprI-OprF (D), suspended in 100 µl of "ABM 2 complete" as adjuvant (Sebak, Aidenbach) on day 0. Booster injections were given with an equal amount of antigen suspended in 100 µl Al(OH)$_3$ on days 14, 28 and 42. On day 49 animals were bled from the tail vein for serum collection to determine antibody titers in the pooled sera of 7–10 mice from each group. Four days later, all the animals received immunosuppressive treatment. For immunosuppression, mice received three injections of 150 µg cyclosphosphamide (Serva, Heidelberg, Germany) per g of body weight in 0.25 ml of phosphate-buffered saline (PBS) on days 53, 55, 57. On day 58, each antigen group was divided into 4 subgroups, I, II, III, IV, containing 16–17 animals per subgroup. The mice of groups A–D received introperitoneally either $5\times10^1$ (subgroup I), 5×10² (subgroup II), 5×10³ (subgroup III) or 5×10⁴ (subgroup IV) CFU of *P. aeruginosa* serogroup 1. 15 additional nonimmunized mice underwent only immunosuppression without bacterial challenge. This control group was used to confirm the state of leukopenia and to exclude nonspecific infections. All surviving animals were monitored for 10 days after infection.

Expression and purification of recombinant OprF-OprI in yeast: For expression of the *P. aeruginosa* outer membrane proteins in *S. cerevisiae* the yeast/*E. coli* shuttle vector pYepsec1 (Baldari, C. et al. (1987) EMBO. J. 6, pp. 229–234) was used. This plasmid expresses polypeptides fused to the signal sequence of the *Kluyveromyces lactis* killer toxin. The NcoI/HindIII DNA fragment from PGEX-OprF-OprI, which codes for the OprF-OprI hybrid protein, was isolated, and cloned into pYepsec1, cut with BamHI and HindIII (yielding pYepsec1-F-I). The NcoI and BamHI sites were turned into blunt ends with Klenow enzyme before ligation, whereas the HindIII site was not treated. The soluble OprF-OprI hybrid protein expressed in yeast was purified by affinity chromatography, using a monoclonal antibody directed against epitope D1. The MAb was coupled to BrCN activated sepharose 4B (Pharmacia, Freiburg, Germany), in accordance with the instructions of the manufacturer. Yeast extracts in PBS were loaded onto the column, unspecific bound material was eluted with 0.1 M glycin pH 9.0 buffer containing 0.5 M NaCl. Elutions of OprI-OprF hybrid protein was carried out in 0.1 M glycin buffer, pH 11.0. The column was regenerated by washing with 0.1 M glycin, pH 2.5, followed by washing with PBS.

Production of specific immunoglobulins and passive immunization: Rabbits were immunized three times with 100 µg of purified recombinant OprF-OprI isolated from *S. cerevisiae* cell extracts (or with cell extracts from *S. cerevisiae* alone as controls) emulsified in incomplete Freund adjuvant on days 0, 14 and 28. On day 38, blood samples were obtained and allowed to clot overnight at 4° C. The serum was removed, centrifuged and stored at −20° C. in groups of 30 female SCID mice (18–20 g, Bomholtgard, Denmark), every animal in the group received either 0.5 ml of rabbit anti OprF-OprI serum or 0.5 ml of rabbit anti yeast serum. As an additional control, the animals in one group received 0.5 ml of normal saline. Those in one additional group were injected with 0.5 ml of rabbit serum against heat inactivated cells of serogroup 1 of *P. aeruginosa*. After 3 hours, the animals of groups 1–6 were subdivided into 5 subgroups (a–e), receiving 0.5 ml of *P. aeruginosa* serogroup 1 suspension (10¹, 10², 10³, 10⁴, 10⁵ CFU/ml suspended in mucin respectively. The surviving animals were observed for 1 week. 5 g mucin (Sigma, Taufkirchen, Germany) were suspended in 100 ml of distilled water, treated for 10 min. with an Ultra Turrax blender, passed through a sieve and autoclaved for 15 min at 120° C. Shortly before use, the solution was adjusted to pH 7.2–7.4 with sterile 1 N NaOH.

EXAMPLES

Example 1: Epitope mapping of OprF

In order to identify amino acid sequence sections of OprF representing B-cell epitopes as a rational basis for the choice of an Opr-based *P. aeruginosa* vaccine, we prepared monoclonal antibodies against a recombinant protein representing amino acids 58 to 350 of OprF. Binding of the MAbs was analyzed with a series of recombinant subfragments of OprF expressed in *E. coli*. The MAbs discriminated between 5 different regions: aa 190–213 (D1), aa 212–240 (D2, SEE 1), aa 239–250 (D3), aa 284–316 (D4) and aa 332–350 (D5, SEE 4). The C-terminal part of OprF between aa 190 and aa 350 seemed therefore to cover most of the B cell epitopes of OprF. To further analyze the epitopes, synthetic peptides related to the above defined amino acid sections were prepared and conjugated to KLH. Polyclonal antisera against these peptides were raised in rabbits. Table 1 shows that peptides D1–D5 were recognized by the corresponding polyclonal antisera. The peptides D1, D2, D4 and D5 reacted with monoclonal antibodies, and peptides D2, D3, D4 and D5 were also recognized by polyclonal antibodies raised against recombinant OprF, thus confirming that these 5 epitopes are B-cell derived. Antisera raised against D3, D4 and D5 recognized OprF in Western blot analysis, but viable *P. aeruginosa* cells showed positive fluorescence only after incubations with the antisera raised against D2 and D5. These two epitopes therefore seem to be surface-exposed. Additional MAbs were identified which did not react with any of the synthetic peptides, but recognized GST-OprF and further recombinant subfragments, leading to two additional epitopes, D6 and D7, which correspond to amino acid residues 240–316 and 190–250 respectively. Therefore, the region from amino acid 190 to amino acid. 350 of OprF was considered to include important antigenic regions, and we decided to ascertain whether recombinant proteins carrying these epitopes are able to confer protection in animal models.

Example 2: Epitope mapping of OprI

With the MAbs 2A1, 6A4 and 5B4 raised against native OprI, two different epitopes have been characterized (Finke, et al. (1991), infect. Inmmun. 59, pp. 1251–1254). MAb 2A1, which had shown protective ability against *P. aeruginosa* infection, recognized the N-terminal located epitope. Subsequent studies showed that 2A1 only binds if the entire amino acid sequence from amino acid 21 to amino acid 83 is expressed. For the construction of recombinant OprI antigens as means of a subunit vaccine, the complete amino acid region 21–83 was therefore considered to be the most adequate antigen.

Example 3: Expression of Oprs in *E. coli*

Figure 1:
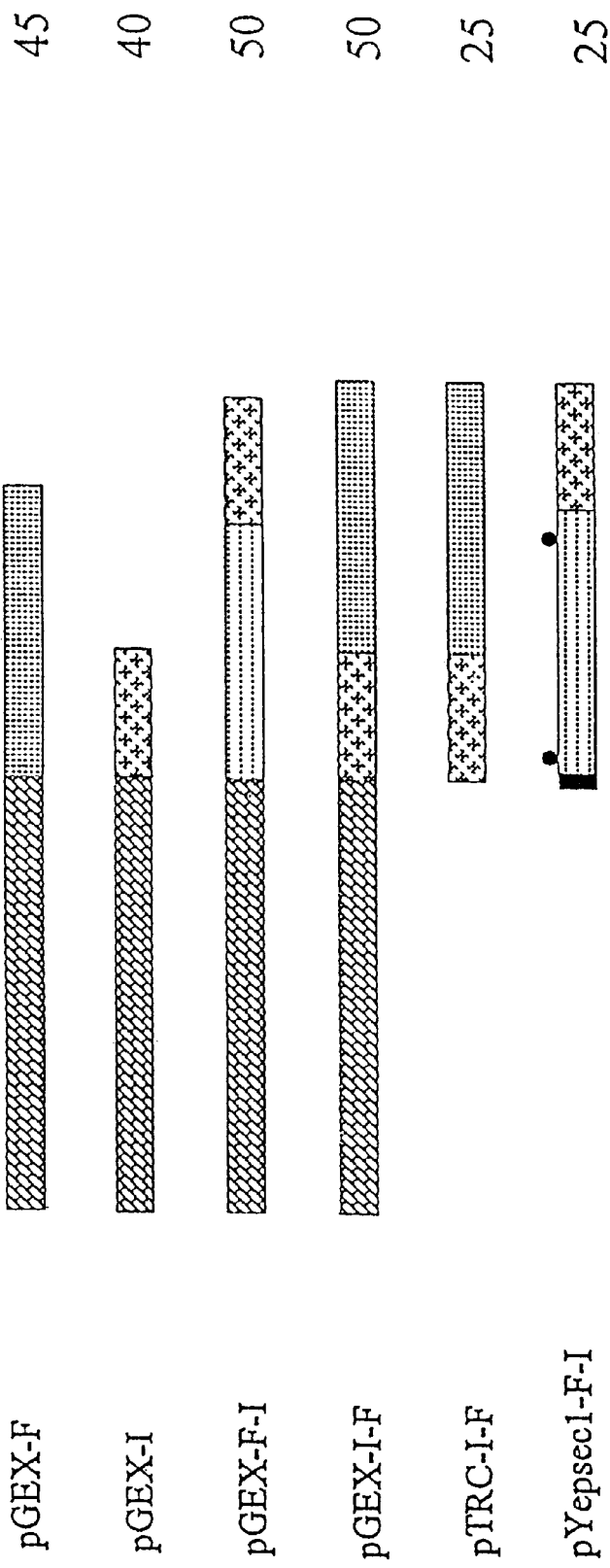
FIG. 1 is a schematic overview of the constructed recombinant fusion proteins of outer membrane proteins of *P. aeruginosa*. For expression in *E. coli* K12, the vector pGEX-2a, which codes for glutathion-S-transferase was used.

The efficacy of a single outer membrane protein of *P. aeruginosa* in a vaccine against *P. aeruginosa* infection might be improved by coexpression of the fused epitopes of two different Oprs. Four different glutathion-S-transferase-fusion proteins were expressed in *E. coli* in large amounts: GST-OprF$_{(aa\ 190-350)}$, GST-OprI$_{(aa\ 21-83)}$, GST-OPrF$_{(aa\ 190-342)}$-OPrI$_{(aa\ 21-83)}$ and GST-OPrI$_{(aa\ 21-83)}$-OPrF$_{(aa\ 190-350)}$ (FIG. 1). The recombinant proteins could be about 80% purified by affinity chromatography on immobilized glutathion. Western blot analysis of the four recombinant products with the OprI specific MAbs 6A4 and 2A1 and different OprF specific MAbs directed against the epitopes D1, D2, D4, D5, D5, D6 and D7 showed that the MAb specific epitopes were expressed by the recombinant fusion proteins.

Example 4: Active immunization with *E. coli* derived fusion proteins

Mice were immunized four times at two week intervals with 100 µg of recombinant GST linked fusion protein, or GST only, suspended in adjuvant "ABM complete". The antibody titers, each from the pooled sera of 8–10 mice, were analyzed by ELISA as well by Western blotting for binding activity against *P. aeruginosa,* and by ELISA against peptides D1–D5.

FIG. 2 shows that specific antibody titers against *P. aeruginosa* were obtained in all immunized groups up to serum dilutions 1:15625. Western blot analysis of the sera with. *P. aeruginosa* polypeptides showed specific staining of OprI as well as of OprF by sera from all immunized groups. No staining of OprI or OprF was observed in the GST immunized control group. Further analysis of the sera against peptides D1–D5 (FIG. 3). showed that, in GST-OprF-OprI as well as GST-OprI-OprF immunized animals, peptides D5 and D4 predominated. In order to test whether the induced antibodies against outer membrane fusion proteins protect mice against *P. aeruginosa* infection, mice received three doses of cyclophosphamide for immunosuppression. Leukocyte counts determined in peripheral blood samples of 15 non-immunized control animals dropped to mean levels below 400/$\mu$l. One day later, the animals were challenged with either $5\times10^1$, $5\times10^2$, $5\times10^3$ or $5\times10^4$ CFU of *P. aeruginosa* serogroup 1. Survival of the animals was registered for one week. FIG. 4 and Table 2 show the survival rates of the animals after 4 different challenge doses and the $LD_{50}$ values for each of the vaccines, calculated by probit regression analysis. For groups immunized with GST only or with GST-OprI-OprF, $LD_{50}$ values as low as 1.58 and 2.65 were calculated. Simultaneous vaccination with a mixture of GST-OprI and GST-OprF induced an increase of the $LD_{50}$ value to 83.3 CFU. This difference, however, was found to be not statistically significant. In contrast, after vaccination with the, hybrid GST-OprF-OprI a highly significant shift of the $LD_{50}$ value towards 1540 CFU was calculated ($p\leq0.001$). Compared to the GST immunized controls, a protection value of 962 was calculated for the GST-OprF-OprI group. These results could be confirmed ($p\leq0.001$) in an identically designed second experiment.

Analysis of the data by the proportional hazard model and calculation of the reduction of the rise ratios induced by the different vaccine preparations is shown in Table 2. Vaccination with GST-OprF-OprI reduced the risc ratio highly significantly ($p\leq0.0001$) to a value of 0.3 compared to the GST immunized controls. Even for a challenge dose of $5\times10^3$ CFU, a significant ($p\leq0.0019$) reduction of the risc ratio to a value of 0.69 was calculated by backward elimination for the GST-OprF-OprI vaccinated group, with reference based on GST, GST-OprF+GST-OprI, GST-OprI-OprF immunized groups, and doses one and two ($5\times10^1$ and $5\times10^2$).

Example 5: Expression of OprF-OprI in yeast

For the expression of the OprF-OprI hybrid protein without an additional fusion component we chose as an alternative host cell *Saccharomyces cerevisiae* and as plasmid pYepsec1. OprF-OprI contained in pYepsec1-F-I (FIG. 1) was expressed only in minute amounts in *S. cerevisiae*. Since OprF as well as OprI are exported in Pseudomonadaceae through the periplasmic space, we tried to copy the export in *S. cerevisiae*. To this end, the OprF-OprI hybrid protein was fused to the secretion signal sequence of the killer toxin (kt) of the yeast *Kluyveromyces lactis*. The tripartite hybrid protein kt. OprF-OprI encoded by pYepsec1-F-I (FIG. 1) now consists of the following polypeptide stretches: first there are the 16 amino acids of the yeast secretion signal sequences, followed by 9 amino acids encoded by a DNA linker and then followed by the OprF specific polypeptide stretch from amino acids 190–342 and an OprI peptide including amino acids 21–83. The OprF specific polypeptide carries the potential glycosylation site asparagine-x-threonine (see FIG. 1) twice. These glycosylation sites should be recognizable if the fusion protein enters the secretionary pathway. Upon fusion to the killer toxin leader sequence, OprF-OprI was detected in yeast cell extracts by Western blot analysis, when expressed under induced condition of the $UAS_{GAL}$/CYC1 promoter, but no secreted antigen was detected in the culture broth.

The OprF-OprI fusions protein expressed in yeast did not migrate as a sharp band in SDS polyacrylamide gels, but showed a heterogeneous distribution, appearing in several smearing bands. This indicates posttranslational modification by N-glycosylation. Incubation of the recombinant *P. aeruginosa* antigen with endoglycosidase F resulted in the appearance of a sharp band of lower molecular weight, indicating the entering of OprF-OprI into the secretionary pathway when fused to the killer toxin leader sequence, and the glycosylation of at least one of the two potential glycosylation sites.

Example 6: Passive immunization with antibodies against yeast-derived OprF-OprI

The recombinant Pseudomonas antigen was enriched from the supernatants of yeast cell extracts by ammonium salt precipitation and immunoaffinity chromatography, using an anti OprF mouse monoclonal antibody directed against epitope D1. Rabbits were then immunized three times with the antigen, and sera were collected from the animals. Whereas the preimmune sera did not show any reactivity with either *P. aeruginosa* OprF or OprI, the sera from the immunized rabbits reacted specifically with the outer membrane proteins OprF and OprI from the three different ATCC strains of *P. aeruginosa,* as well with the three different clinical isolates of *P. aeruginosa* tested. The protective efficacy of these sera was tested in SCID mice for defence against a lethal challenge with *P. aeruginosa*. As shown in Table 3, mice injected with the control anti-yeast serum were not protected against infection even at a challenge dose of $5\times10^1$ (Table 3, group 1). On the other hand, mice which received the OprF-OprI specific rabbit serum were fully protected against a $5\times10^2$ CFU challenge dose of *P. aeruginosae* (Table 3, group 3), and 40% survival was observed after challenge with $5\times10^3$, CFU. As an additional control, protection by rabbit serum induced against LPS of the challenge strain, *P. aeruginosa* serogroup 1, was tested. Up to a challenge dose of $5\times10^3$, 100% of the animals protected with LPS specific serum survived (Table 3, group 5). No survival could be observed in this group, after a 10-fold higher challenge dise of $5\times10^4$. Statistical analysis was used to compare the protective doses of OprF-OprI specific serum, of LPS specific serum, and the anti-yeast control group for protection against *P. aeruginosa* infection. The results showed an 85-fold increase in potency of the OprF-OprI serum in comparison with the anti yeast serum ($p\leq0.002$—see Table 3, group 3). As against this, a 325 higher potency was calculated for the LPS specific serum than for the anti-yeast serum ($p\leq0.001$).

TABLE 1

Characterization of B cell epitopes of *P. aeruginosa* OprF

| peptide | OprF specific aa region | MAbs* | rabbit anti OprF ELISA (against peptide) | rabbit antisera** ELISA (against peptide) | rabbit antisera** Western blot (against OprF) | rabbit antisera** immunofluorescence of intact *P. aeruginosa**** |
|---|---|---|---|---|---|---|
| D1 | 190–213 | + | – | + | – | – |
| D2 | 212–240 | + | + | + | – | + |
| D3 | 239–250 | – | + | + | + | – |
| D4 | 284–216 | + | + | + | + | – |
| D5 | 332–350 | + | + | + | + | + |

*MAbs were induced in mice against a recombinant protein representing amino acids 58-350 of OprF, binding to peptides D1–D5 was analyzed by ELISA.
**Rabbits were immunized with peptides linked to KLH.
***estimated with *P. aeruginosa* serogroup 11 (ATCC 33359).

TABLE 2

Statistical analysis of survival of mice*

| | Vaccine | | | |
|---|---|---|---|---|
| | GST | GST-OprF + GST-OprI | GST-OprF – OprI | GST-OprI – OprF |
| $LD_{50}$ | 1.58 | 83.34 | 1540++ | 2.65 |
| Shift.$LD_{50}$** | 1 | 52 | 962 | 1.7 |
| Risk Ratio*** | 1 | 0.732 | 0.344+++ | 0.889 |

*mice were vaccinated with the indicated GST linked recombinant Oprs or GST as control.
**$LD_{50}$ values were calculated by probit analysis (Finney, D. J. (1971), Probit analysis, Cambridge University Press, Cambridge).
++$P < 0.05$ versus GST group.
+++$P < 0.0001$ versus GST group.
***Risk ratios were calculated by the proportional hazard model (Lawless, J. F. (1982), Statistical Methods for Lifetime Data, John Wiley & Sons, New York) with reference based on GST group.

TABLE 3

Protection against *P. aeruginosa* infection in SCID mice by rabbit anti OprF – OprI sera Surviving animals after transfer of specific rabbit serum before challenge, group no. (n = 5)

| challenge dose** (CFU) | 1 yeast* control | 2 yeast* control 1:10 | 3 OprF – OprI* | 4 OprF – OprI* 1:10 | 5 *P. aeruginosa**** | 6 challenge control | 7 mucin control |
|---|---|---|---|---|---|---|---|
| $5 \times 10^0$ | 5 | 5 | 5 | 5 | 5 | 1 | |
| $5 \times 10^1$ | 1 | 1 | 5 | 4 | 5 | 0 | |
| $5 \times 10^2$ | 1 | 0 | 5 | 2 | 5 | 0 | |
| $5 \times 10^3$ | 0 | 1 | 2 | 0 | 5 | 0 | |
| $5 \times 10^4$ | 0 | 0 | 0 | 0 | 0 | 0 | |
| mucin | | | | | | | 5 |

*Rabbit serum of animals immunized with the indicated antigen.
**Female C.B-17 scid/scid mice (SCID) were challenged intraperitoneally with the indicated colony forming units (CFU) of *P. aeruginosa* serogroup 1 suspended with 0.5 ml of mucin.
***rabbit serum of animals immunized with *P. aeruginosa* serogroup 1. Statistical analysis (probit analysis for parallel line model); group 1 versus group 3: 85-fold increase in potency, significance (chi-square), 0.002. Group 1 versus group 5; 325-fold increase in potency, significance 0.001.

We claim:

1. A hybrid protein comprising the *Pseudomonas aeruginosa* outer membrane protein I which is fused at its amino terminal end to the carboxy terminal end of a carboxy terminal portion of the *Pseudomonas aeruginosa* outer membrane protein F, said carboxy terminal portion comprising the sequence from aa 190 to aa 350.

2. The hybrid protein as claimed in claim 1, wherein said carboxy terminal portion is the sequence from aa 190 to aa 342.

3. A hybrid protein comprising the *Pseudomonas aeruginosa* outer membrane protein I which is fused at its amino terminal end to the carboxy terminal end of a carboxy terminal portion of the *Pseudomonas aeruginosa* outer membrane protein F, said carboxy terminal portion comprising at least one surface-exposed B-cell epitope selected from the group consisting of SEE 1, SEE 2, SEE 3 and SEE 4.

4. A vaccine comprising a hybrid protein as claimed in claim 1.

5. A vaccine comprising a hybrid protein as claimed in claim 2.

6. A vaccine comprising a hybrid protein as claimed in claim 3.

* * * * *